(12) United States Patent  
Clubb

(10) Patent No.: US 7,695,491 B2  
(45) Date of Patent: Apr. 13, 2010

(54) RAPID EXCHANGE CATHETERS WITH TANDEM LUMENS

(75) Inventor: Thomas L. Clubb, Hudson, WI (US)

(73) Assignee: ev3 Inc., Plymouth, MN (US)

( * ) Notice: Subject to any disclaimer, the term of this patent is extended or adjusted under 35 U.S.C. 154(b) by 1579 days.

(21) Appl. No.: 10/724,816

(22) Filed: Dec. 1, 2003

(65) Prior Publication Data

US 2005/0119686 A1 Jun. 2, 2005

(51) Int. Cl.
*A61M 29/00* (2006.01)

(52) U.S. Cl. .................................................. 606/200

(58) Field of Classification Search ............... 604/103, 604/93.01, 101.01, 103.04, 101.05; 606/200; 600/564–568

See application file for complete search history.

(56) References Cited

U.S. PATENT DOCUMENTS

| | | | | | |
|---|---|---|---|---|---|
| 4,774,949 | A | * | 10/1988 | Fogarty | 606/108 |
| 4,836,204 | A | * | 6/1989 | Landymore et al. | 606/215 |
| 4,946,466 | A | * | 8/1990 | Pinchuk et al. | 606/194 |
| 4,958,634 | A | * | 9/1990 | Jang | 606/194 |
| 4,979,951 | A | * | 12/1990 | Simpson | 600/565 |
| 5,069,662 | A | * | 12/1991 | Bodden | 604/5.01 |
| 5,267,958 | A | | 12/1993 | Buchbinder et al. | |
| 5,290,247 | A | | 3/1994 | Crittenden | |
| 5,439,445 | A | | 8/1995 | Kontos | |
| 5,462,530 | A | | 10/1995 | Jang | |
| 5,507,731 | A | | 4/1996 | Hernandez et al. | |
| 5,569,199 | A | | 10/1996 | Solar | |
| 5,571,094 | A | | 11/1996 | Sirhan | |
| 5,662,671 | A | * | 9/1997 | Barbut et al. | 606/170 |

(Continued)

FOREIGN PATENT DOCUMENTS

EP 0 321 912 A1 6/1989

(Continued)

OTHER PUBLICATIONS

Apr. 11, 2005 Notification of Transmittal of the International Search Report and the Written Opinion of the International Searching Authority, or the Declaration in PCT/US2004/039443 (18 pages).

(Continued)

*Primary Examiner*—Kevin C Sirmons
*Assistant Examiner*—Elizabeth R Moulton
(74) *Attorney, Agent, or Firm*—Popovich, Wiles & O'Connell, P.A.

(57) ABSTRACT

A catheter having a proximal portion and a distal portion comprising: a first elongate tubular body; a second elongate tubular body; and an elongate member joining the first and second elongate bodies. The first elongate tubular body is disposed proximal and tandem to the second elongate tubular body, and the first and second tubular bodies are permanently disposed so that the first and second tubular bodies are not adjacent to each other. The catheter also comprises a third elongate tubular body, at least the proximal portion of the third elongate tubular body being disposed within the lumen of the first elongate tubular body, the third elongate tubular body being slidable within the lumen of the first elongate tubular body, and the distal portion of the third elongate tubular body being able to be disposed in the lumen of the second elongate tubular body.

67 Claims, 14 Drawing Sheets

U.S. PATENT DOCUMENTS

| | | |
|---|---|---|
| 5,669,880 A | 9/1997 | Solar |
| 5,769,816 A | 6/1998 | Barbut et al. |
| 5,935,114 A | 8/1999 | Jang et al. |
| 6,056,722 A | 5/2000 | Jayaraman |
| 6,290,673 B1 * | 9/2001 | Shanley .............. 604/102.02 |
| 6,312,406 B1 | 11/2001 | Jayaraman |
| 6,447,501 B1 | 9/2002 | Solar et al. |
| 6,562,024 B2 | 5/2003 | Alvarez de Toledo et al. |
| 6,592,548 B2 | 7/2003 | Jayaraman |
| 6,743,208 B1 * | 6/2004 | Coyle .................. 604/164.13 |
| 6,887,257 B2 | 5/2005 | Salahieh et al. |
| 7,226,464 B2 * | 6/2007 | Garner et al. .............. 606/200 |
| 7,235,061 B2 | 6/2007 | Tsugita |
| 2003/0078519 A1 | 4/2003 | Salahieh et al. |
| 2003/0109886 A1 | 6/2003 | Keegan et al. |
| 2003/0125751 A1 * | 7/2003 | Griffin et al. ............. 606/108 |
| 2003/0171770 A1 * | 9/2003 | Kusleika et al. ............. 606/200 |

FOREIGN PATENT DOCUMENTS

| | | |
|---|---|---|
| WO | WO 96/01591 | 1/1996 |
| WO | WO 97/00094 | 1/1997 |
| WO | WO 03/034941 A1 | 5/2003 |

OTHER PUBLICATIONS

Notification Concerning Transmittal of International Preliminary Report on Patentability (Chapter I of the Patent Cooperation Treaty) dated Jun. 15, 2006 (11 pages).

* cited by examiner

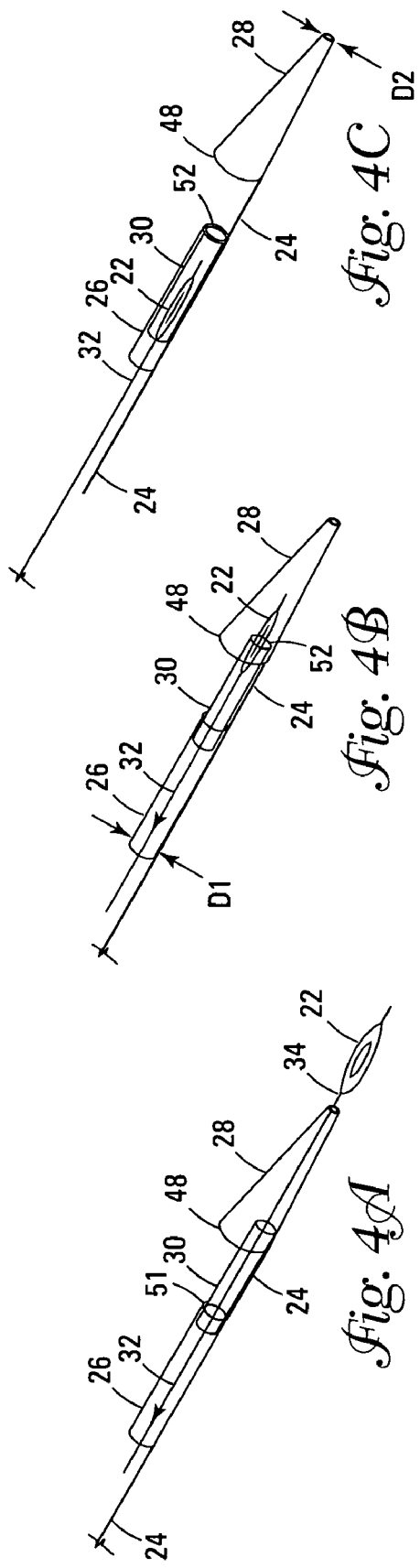

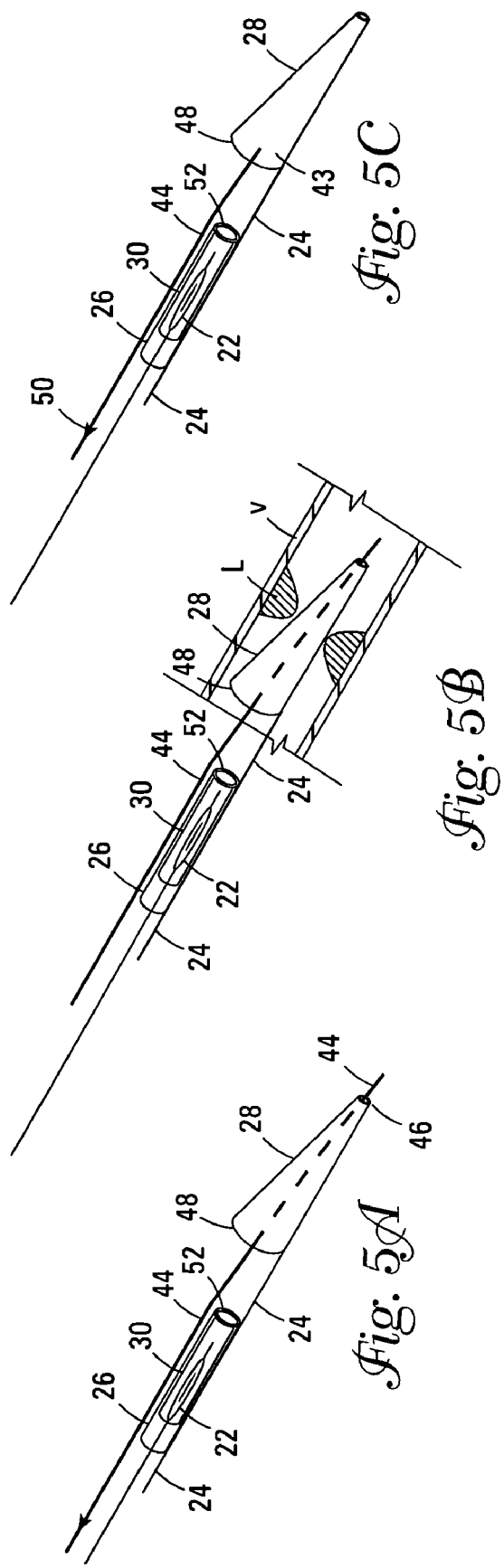

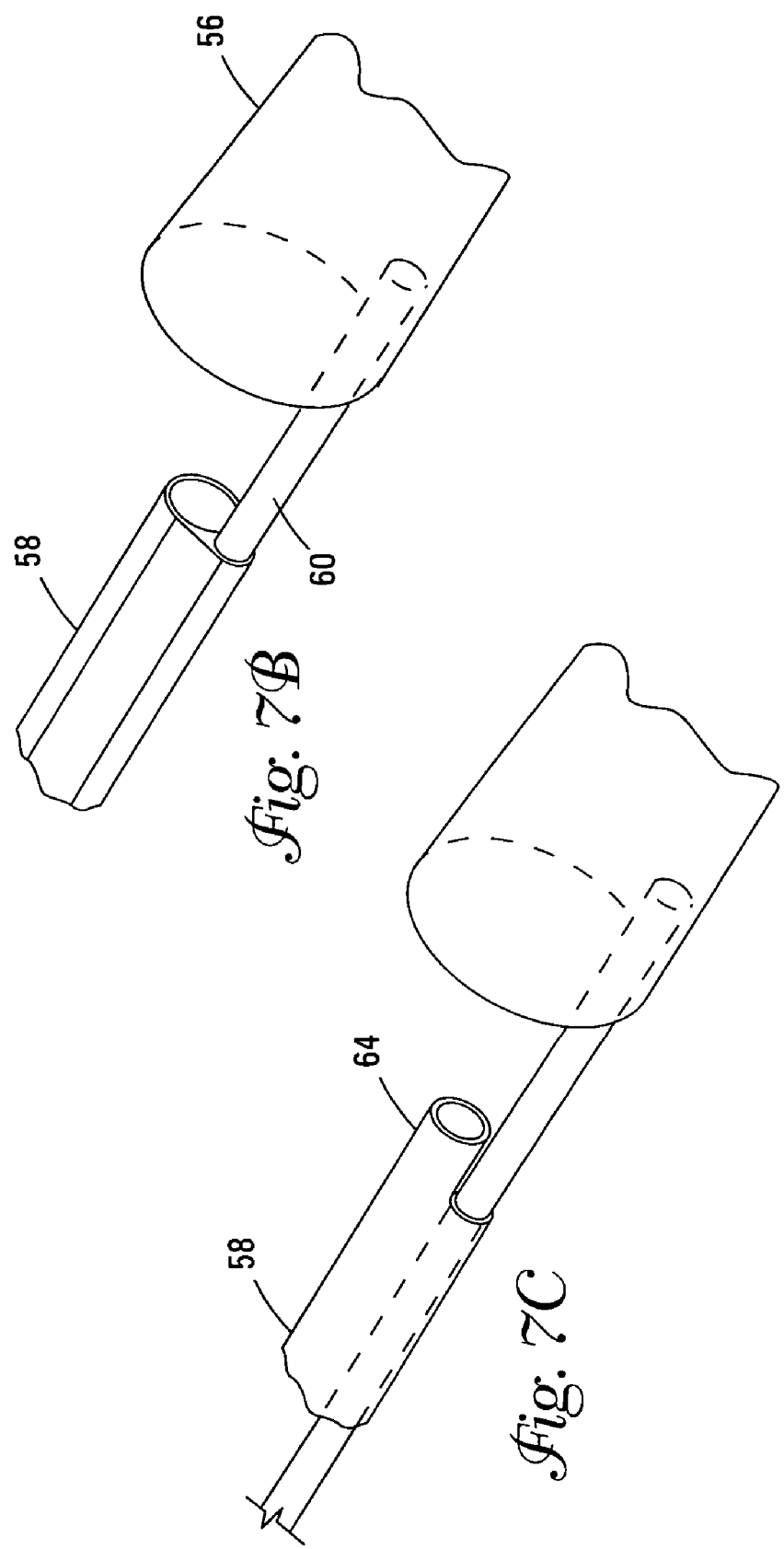

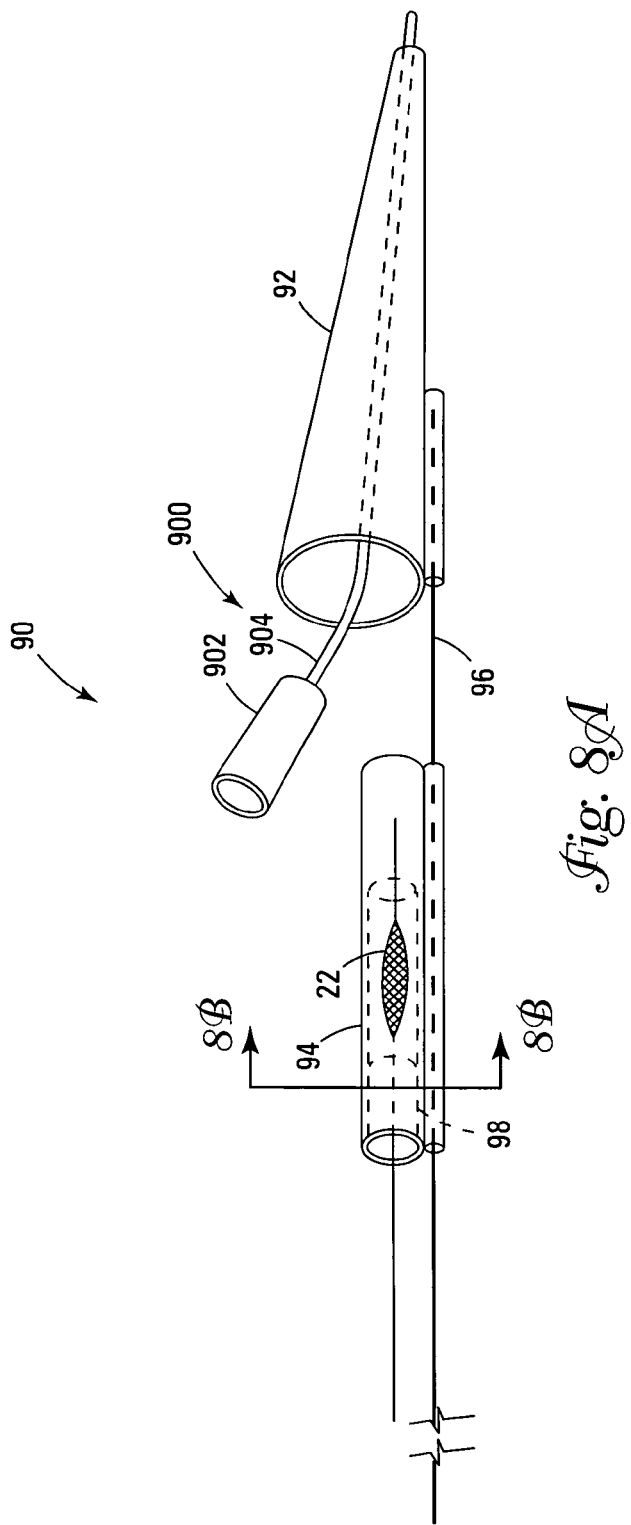
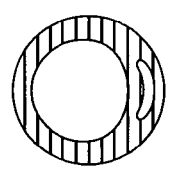
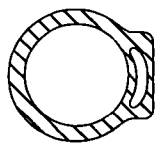

RAPID EXCHANGE CATHETERS WITH TANDEM LUMENS

FIELD OF THE INVENTION

This invention relates to devices used in a blood vessel or other lumen in a patient's body. In particular, the present invention relates to catheters having tandem lumens.

BACKGROUND OF THE INVENTION

Coronary vessels, partially occluded by plaque, may become totally occluded by thrombus or blood clot causing myocardial infarction, angina, and other conditions. Carotid, renal, peripheral, and other blood vessels can also be restrictive to blood flow and require treatment. A number of medical procedures have been developed to allow for the removal or displacement (dilation) of plaque or thrombus from vessel walls to open a channel to restore blood flow and minimize the risk of myocardial infarction. For example, atherectomy or thrombectomy devices can be used to remove atheroma or thrombus. In cases where infusion of drugs or aspiration of thrombus may be desired, infusion or aspiration catheters can be placed near the treatment site to infuse or aspirate. In cases where the treatment device can be reasonably expected to shed emboli, embolic protection devices can be placed near the treatment site to capture and remove emboli. In other cases, a stent is placed at the treatment site. Both embolic protection devices and stents can be placed in or near the treatment site using delivery catheters.

In percutaneous transluminal coronary angioplasty (PTCA), a guide wire and guide catheter are inserted into the femoral artery of a patient near the groin, advanced through the artery, over the aortic arch, and into a coronary artery. An inflatable balloon is then advanced into the coronary artery, across a stenosis or blockage, and the balloon inflated to dilate the blockage and open a flow channel through the partially blocked vessel region. One or more stents may also be placed across the dilated region or regions to structurally maintain the open vessel. Balloon expandable stents are crimped onto a balloon in the deflated state and delivered to the lesion site. Balloon expansion expands the stent against the lesion and arterial wall. Alternatively, self expanding stents can be restrained in a sheath, delivered to the treatment site, and the sheath removed to allow expansion of the stent.

Embolic protection devices have been developed to prevent the downstream travel of materials such as thrombi, grumous, emboli, and plaque fragments. Devices include occlusive devices and filters. Occlusive devices, for example distal inflatable balloon devices, can totally block fluid flow through the vessel. The material trapped by the inflatable devices can remain in place until removal using a method such as aspiration. However, aspiration cannot remove large particles because they will not fit through the aspiration lumen. Also, aspiration is a weak acting force and will not remove a particle unless the tip of the aspirating catheter is very close to the particle to be removed. During the occlusion, the lack of fluid flow can be deleterious. In coronary applications, the lack of perfusing blood flow can cause angina. In carotids, seizure can result from transient blockage of blood flow. In both coronaries and carotids, it is not possible to predict who will suffer from angina or seizure due to vessel occlusion. If a procedure starts with an occlusive device, it may be necessary to remove it and start over with a filter device.

Occlusive embolic protection devices can also be placed proximal to the treatment site. Debris generated at or near the treatment site will not be transported from the treatment site if a proximal occlusive device substantially stops blood flow through the vessel. The material generated during treatment can remain in place until removal using a method such as aspiration. Generally, proximal occlusive embolic protection devices suffer from many of the same limitations as distal occlusive embolic protection devices.

Other embolic protection devices are filters. Filters can allow perfusing blood flow during the emboli capture process. The filters can advance downstream of a site to be treated and expand to increase the filter area. The filter can capture emboli, such as grumous or atheroma fragments, until the procedure is complete or the filter is occluded. When the filter reaches its capacity, the filter may then be retracted and replaced.

Embolic protection devices can be delivered over wires and within guide catheters. The embolic protection methods are normally practiced ancillary to another medical procedure, for example PTCA with stenting or atherectomy. The embolic protection procedure typically protects downstream regions from emboli resulting from practicing the therapeutic interventional procedure. In the example of PTCA, the treating physician must advance a guide wire through the aorta, over the aortic arch, and into a coronary ostium. Advancing the guide wire through tortuous vessels from a femoral artery approach can be difficult and vary with both the patient and the vessel site to be treated. Guide wires are typically selected by the treating physician, based on facts specific to the patient and therapeutic situation, and also on the training, experiences, and preferences of the physician. In particular, a physician may have become very efficient in using a specific guide wire to identify the left coronary ostium and then advance a balloon catheter over the positioned guide wire. The efficacy of the procedure may depend on the physician being able to use a favored guide wire.

In the example PTCA procedure, a guide catheter extends proximally from the patient's groin area, and may be about 100 centimeters long. A 320 cm guidewire is placed into the guide catheter and extended distal of the guide into a coronary vessel, leaving about a 200 cm long guide wire proximal region extending from the guide catheter. The embolic protection device delivery catheter, nominally about 130 cm in length, can advance over the guide wire and within the guide catheter, until a length of guide wire extends from both the guide catheter and delivery catheter. The guide wire can then be retracted and removed from the patient. In some methods, the embolic protection device then advances through and out of the positioned delivery catheter, to the target site to be protected or filtered. In other methods, delivery is accomplished by disposing the embolic protection filter device within the delivery catheter distal region, and advancing the delivery catheter and embolic protection device together within the guide catheter, optionally over the guide wire, and deploying the filter by retracting the delivery catheter while maintaining the position of the filter, thus forcing the filter distally out of the delivery catheter.

Advancement of the delivery catheter over a single length, nominally 170 cm long guide wire presents a problem. The treating physician can only advance the filter delivery catheter about 40 cm over the guide wire until the delivery catheter advances into the patient and the guide wire is inaccessible within the delivery catheter. The guide wire position should be controlled at all times so as to not be dislodged by the advancing delivery catheter from the hard acquired guide wire position within the patient.

One solution to this problem is to use a guide wire at least double the length of the delivery catheter as described above.

A 320 cm long guide wire can extend at least about 150 cm from the patient's groin, having an accessible region exposed at all phases of delivery catheter placement. However, the length of the 320 cm guidewire makes manipulating and rotating the guide wire very difficult for the treating physician. Additional personnel can hold the extra length of the guide wire to prevent the added wire length from falling to the floor, where it would become contaminated. However, not all cardiac catheter laboratories have personnel available to maintain control of the long guide wire. In many labs, the physician is working alone in the sterile field. Advancing a device delivery catheter over a positioned, favored, and short (175 cm) guide wire would be inherently more efficacious than requiring use of an unfamiliar, disfavored, or double length guide wire to position the delivery catheter.

Another alternative catheter design is the monorail or rapid exchange type such as that disclosed in U.S. Pat. No. 4,762,129, issued Aug. 9, 1988, to Bonzel. This catheter design utilizes a conventional inflation lumen plus a relatively short parallel guiding or through lumen located at its distal end and passing through the dilatation balloon. Guide wires used with PTCA balloon catheters are typically 175 cm in length and are much easier to keep within the sterile operating field than 300 to 340 cm guide wires. This design enables the short externally accessible rapid exchange guide wire lumen to be threaded over the proximal end of a pre-positioned guide wire without the need for long guide wires.

Still needed in the art are improved designs for rapid exchange delivery catheters.

SUMMARY OF THE INVENTION

The present invention provides improved multiple lumen delivery/recovery catheters. The catheters are "rapid exchange" or "single operator exchange" catheters.

The invention provides a catheter having a proximal portion and a distal portion comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member joining the first and second elongate bodies. The first elongate tubular body is disposed proximal and tandem to the second elongate tubular body, and the first and second tubular bodies are permanently disposed so that the first and second tubular bodies are not adjacent to each other. The catheter comprises a third elongate tubular body having a proximal portion, a distal portion, a proximal end, a distal end, and a lumen extending between the proximal end and the distal end, at least the proximal portion of the third elongate tubular body being disposed within the lumen of the first elongate tubular body, the third elongate tubular body being slidable within the lumen of the first elongate tubular body, and the distal portion of the third elongate tubular body being able to be disposed in the lumen of the second elongate tubular body.

The invention provides a catheter having a proximal portion and a distal portion comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member joining the first and second elongate bodies. The first elongate tubular body is disposed proximal and tandem to the second elongate tubular body, and the first and second tubular bodies are able to be disposed in a first position so that the first and second tubular bodies are not adjacent to each other and able to be disposed in a second position so that the first and second tubular bodies are adjacent to each other.

The invention also provides a method for positioning a catheter within a patient's blood vessel, the method comprising: providing a catheter described herein; providing a guide wire having a proximal end and a distal end; advancing the guide wire to a target site within the patient's blood vessel; disposing the guide wire proximal end within the lumen of the second elongate tubular body and not within the lumen of the first elongate tubular body; and advancing the catheter over the guide wire to the target site.

It is to be understood that both the foregoing general description and the following detailed description are exemplary and explanatory and are intended to provide further explanation of the invention as claimed.

BRIEF DESCRIPTION OF THE DRAWINGS

FIGS. 4A to 4C are perspective views of the catheter of FIG. 3, showing an embolic protection device being loaded into the catheter.

FIGS. 5A to 5C are perspective views of the catheter of FIG. 3, showing the use of a guide wire.

FIGS. 7A to 7C are perspective views of another embodiment of a catheter of the invention.

FIGS. 8A to 8C are views of an embodiment of a catheter of the invention.

DETAILED DESCRIPTION OF THE PREFERRED EMBODIMENTS

Figure 1:
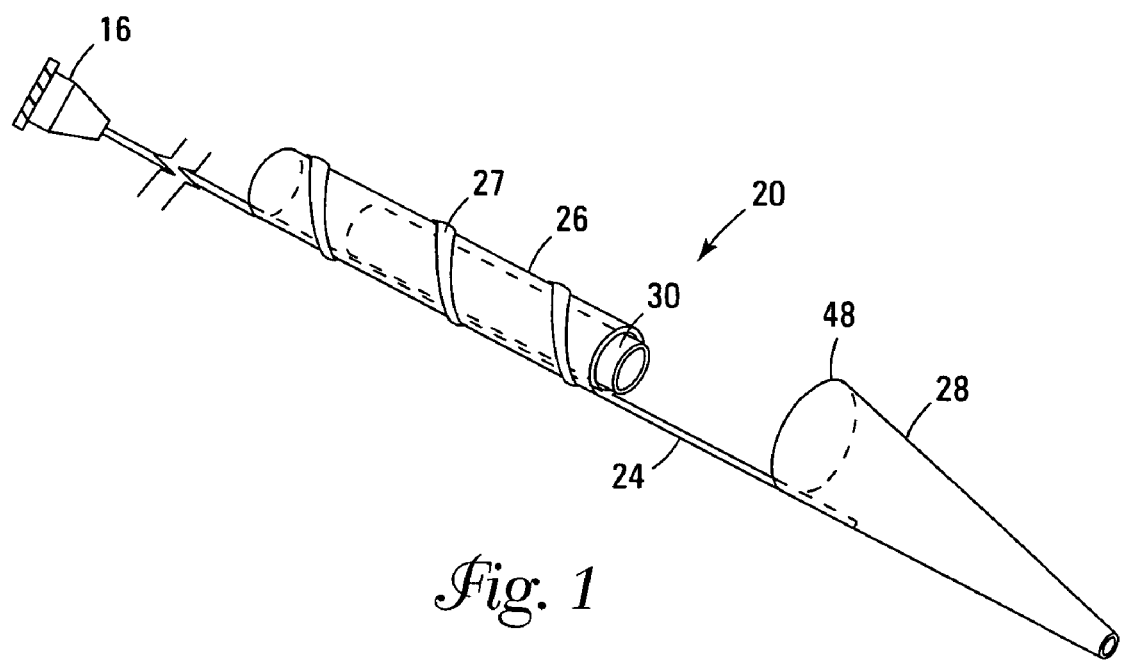
FIG. 1 is a perspective view of an embodiment of a catheter of the invention.

The terms "distal" and "proximal" as used herein refer to the relative position of the guide wire and catheters in a lumen. The most "proximal" point of the catheter is the end of the catheter extending outside the body closest to the physician. The most "distal" point of the catheter is the end of the catheter placed farthest into a body lumen from the entrance site.

The use of the phrases "distal embolic protection device" or "embolic protection device" herein refers to embolic protection devices that are occlusive, diverting, and/or filtering. The term "embolic protection device" is meant to include devices used to protect a target site and located either proximal to, at, or distal to the treatment site.

This invention applies to any catheter used in conjunction with a guide wire or elongate support member for delivery. The concept is universal. Embolic protection device delivery catheters, balloon catheters, and stent delivery catheters with or without a balloon are typical catheters to which the invention can be applied. The concept can also be applied to percutaneous delivery and recovery catheters for atrial appendage occlusion devices, mitral valve remodeling devices, septal defect closure devices, and the like.

The components of the catheters of the invention are made from biocompatible materials such as metals or polymeric materials. If necessary, these metals or polymeric materials can be treated to impart biocompatibility by various surface treatments, as known in the art. Suitable materials include stainless steel, titanium and its alloys, cobalt-chromium-nickel-molybdenum-iron alloy (commercially available under the trade designation ELGILOY™), carbon fiber and its composites, and polymers such as liquid crystal polymers, polyetheretherketone (PEEK), polyimide, polyester, high density polyethylene, PEBAX®, various nylons, and the like. A shape memory or superelastic material such as nitinol or shape memory polymer is also suitable. The size, thickness, and composition of materials are selected for their ability to perform as desired as well as their biocompatibility. It is to be understood that these design elements are known to one of skill in the art.

The material comprising the catheter is preferably at least partially radiopaque. This material can be made radiopaque by plating, or by using core wires, tracer wires, or fillers that have good X-ray absorption characteristics compared to the human body. Marker bands comprised of generally tubular radiopaque metals may be attached to the catheter.

The tip of the catheter may be a generally softer material so as to help prevent damage to a vessel wall as the tip is advanced through the vasculature. Softer materials such as PEBAX®, nylon, rubbers, urethane, silicone, ethylene vinyl acetate, and the like may be attached to the catheter by adhesives, overmolding, heat bonding, solvent bonding, and other techniques known in the art. The tip may have a geometry designed to assist with advancement of the catheter past intraluminal obstructions, such as any of those constructions contained within US 2002/0111649 entitled "Rolled Tip Recovery Catheter", which is hereby incorporated by reference herein in its entirety.

The catheter is generally referred to as an embolic protection delivery/recovery catheter however it is contemplated that the embodiments of the catheters described herein may be used solely for delivery, solely for recovery, or for both delivery and recovery.

The invention provides a catheter having a proximal portion and a distal portion comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member joining the first and second elongate bodies. The first elongate tubular body is disposed proximal and tandem to the second elongate tubular body, and the first and second tubular bodies are permanently disposed so that the first and second tubular bodies are not adjacent to each other. The catheter comprises a third elongate tubular body having a proximal portion, a distal portion, a proximal end, a distal end, and a lumen extending between the proximal end and the distal end, at least the proximal portion of the third elongate tubular body being disposed within the lumen of the first elongate tubular body, the third elongate tubular body being slidable within the lumen of the first elongate tubular body, and the distal portion of the third elongate tubular body being able to be disposed in the lumen of the second elongate tubular body.

In an embodiment of the invention, the proximal portion of the third elongate tubular body is maintained within the lumen of the first elongate tubular body by one or more magnetic or mechanical stops. In another embodiment of the invention, the entire third elongate tubular body is able to be disposed within the lumen of the first elongate tubular body.

In an embodiment of the invention, the first elongate tubular body has an inner diameter and the elongate member has one or more transverse cross-sectional dimensions, each transverse cross-sectional dimension being less than half the inner diameter of the first elongate tubular body. In another embodiment of the invention, each transverse cross-sectional dimension is less than one-quarter of the inner diameter of the first elongate tubular body.

In an embodiment of the invention, the catheter comprises a single elongate member. In another embodiment of the invention, the catheter comprises two or more elongate members. The elongate member may be a curved sheet that partially encircles the first and second tubular bodies. The curved sheet may be made of knit, a weave, or tubular braid that has been folded upon itself to form a sheet.

In an embodiment of the invention, at least a portion of the second elongate tubular body has a non-circular transverse cross-section. In another embodiment of the invention, the second elongate tubular body has one or more holes disposed in its proximal portion. In another embodiment, the second elongate tubular body has a side wall extending between its proximal and distal ends and a port disposed on the side wall.

In an embodiment of the invention, the elongate member is cylindrical. In another embodiment of the invention, the second elongate tubular body has an inner diameter that decreases from the proximal end to the distal end of the second elongate tubular body. In another embodiment of the invention, the second elongate tubular body is funnel-shaped.

In an embodiment of the invention, a proximal shaft is attached to the first elongate tubular body. The proximal shaft may be cylindrical. In an embodiment of the invention, the proximal shaft and the elongate member are formed of one cylindrical element.

The invention provides a catheter having a proximal portion and a distal portion comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member joining the first and second elongate bodies. The first elongate tubular body is disposed proximal and tandem to the second elongate tubular body, and the first and second tubular bodies are permanently disposed so that the first and second tubular bodies are not adjacent to each other. The catheter further comprises a third elongate tubular body having a proximal portion, a distal portion, a proximal end, a distal end, and a lumen extending between the proximal end and the distal end, at least the proximal portion of the third elongate tubular body being disposed within the lumen of the first elongate tubular body, and the third elongate tubular body being slidable within the lumen of the first elongate tubular body. The third tubular body is able to be disposed in a first position so that the second and third tubular bodies are not adjacent to each other and able to be disposed in a second position so that the second and third tubular bodies are adjacent to each other.

The invention provides a catheter having a proximal portion and a distal portion comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member joining the first and second elongate bodies. The first elongate tubular body is disposed proximal and tandem to the second elongate tubular body, and the first and second tubular bodies are able to be disposed in a first position so that the first and second tubular bodies are not adjacent to each other and able to be disposed in a second position so that the first and second tubular bodies are adjacent to each other. In an embodiment of the invention, the first elongate tubular body slides on the elongate member. In another embodiment of the invention, the second elongate tubular body is permanently fixed to the elongate member.

The invention provides an assembly for delivering a catheter, the assembly comprising a guide wire and a catheter.

The catheter of the invention can be selected from a balloon catheter, an infusion/dye-injection/suction catheter, stent delivery catheter, or an embolic protection device delivery catheter. The catheter can comprise an interventional element on the second elongate tubular body.

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent.

FIG. 1 shows a catheter 20 of the invention, including three elongate tubular bodies with an elongate member 24 for axially positioning a first (or proximal) elongate tubular body 26 and a second (or distal) elongate tubular body 28 relative to each other, so that a third (or sliding) elongate tubular body 30 may slidingly traverse between the first elongate tubular body 26 and second elongate tubular body 28. Any of the embodiments of the catheter of the invention may be a delivery/recovery catheter that can be used to both deliver and/or recover a medical device, especially an embolic protection device such as a filter, a diverter, or an occlusive device to a location proximal to, at, or distal to a treatment site. The term "delivery catheter," as used herein, should be understood as including a delivery catheter that can also be used to recover a medical device, especially a particulate containing filter. For convenience throughout this disclosure and the appended claims, the first elongate tubular body 26 may alternatively be referred to as the proximate elongate tubular body, the second elongate tubular body 28 may alternatively be referred to as the distal elongate tubular body, and the third tubular body 30 may alternatively be referred to as the sliding elongate tubular body. An optional wire support structure 27 is disposed about or within the distal portion of the proximal elongate tubular body 26. Optional wire support structure 27 may be a wire, round or flat or other, adhered or heat fused to elongate tubular body 26, roughened (described below), for purpose of providing kink resistance, tensile, and/or column strength.

Proximal elongate tubular body 26 and sliding elongate tubular body 30 can be made from an extruded tube such as PEBAX, polyethylene, nylon, or polyester; alternatively, they can be dip or spray coated on mandrels (subsequently removed) from materials such as polyimide. One or both of the proximal elongate tubular body 26 and sliding elongate tubular body 30 are preferably lined with a slippery material such as PTFE. In a preferred embodiment, the length of proximal elongate tubular body 26 may be limited to only a distal portion of the catheter, as shown. In an alternative embodiment, proximal elongate tubular body 26 may be much longer, extending proximally outside of the patient.

Figure 1A:
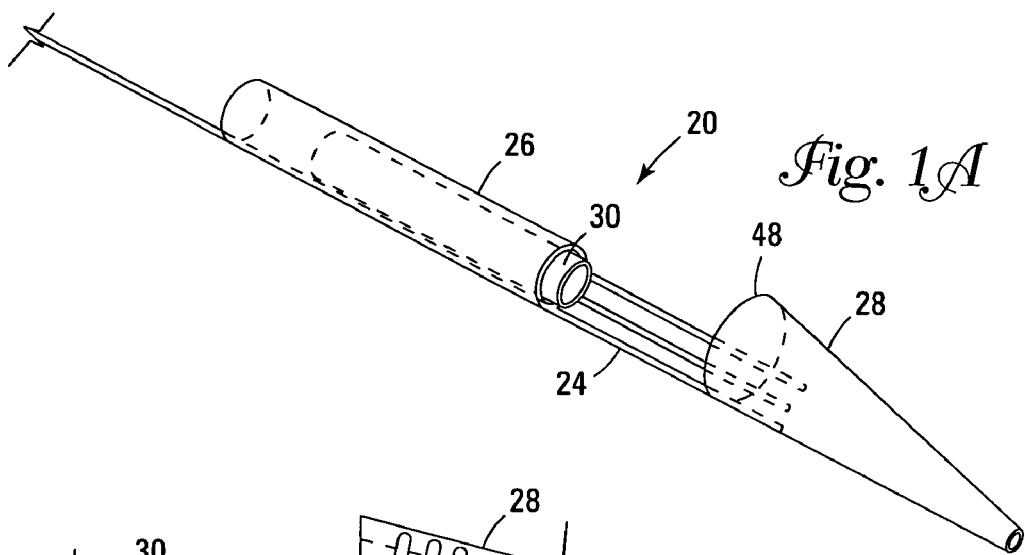
FIGS. 1A to 1H are views of alternative embodiments of catheters of the invention.
Figure 1B:
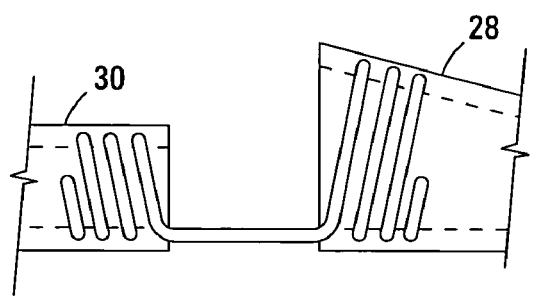
Figure 1C:
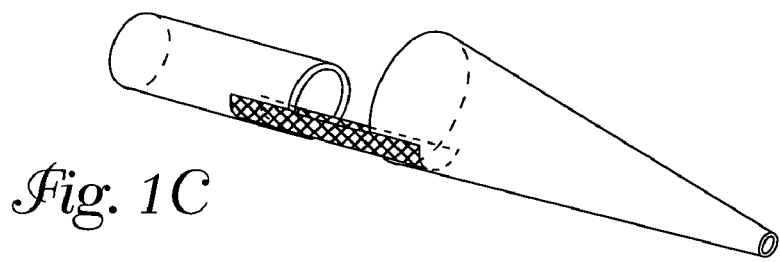
Figure 1D:
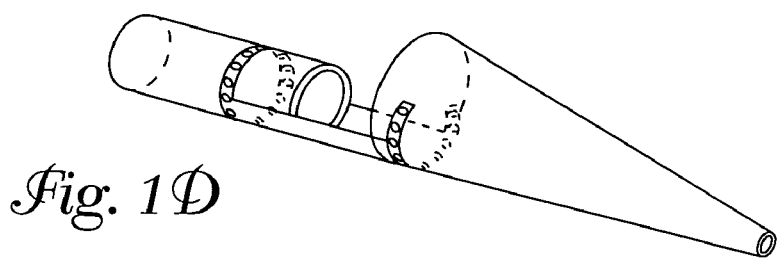
Figure 1E:
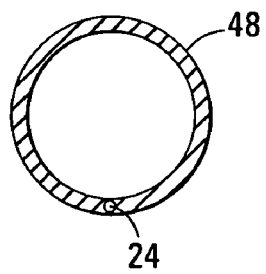

Proximal elongate tubular body 26 and sliding elongate tubular body 30 may have cooperating stops, such as an enlarged region on the slider and a reduced diameter region on the proximal body, so as to limit their relative axial travel. Alternatively, sliding elongate tubular body 30 may have an enlarged distal or proximal end or both to limit proximal slider travel, distal slider travel, or both respectively. Travel of the sliding elongate tubular body 30 may be limited to not contact distal elongate tubular body or the sliding elongate tubular body 30 may be allowed to contact distal elongate tubular body when slid forward. Proximal elongate tubular body 26 or sliding elongate tubular body 30 or both may have a soft distal end or may be tapered at one or both ends. The sliding elongate tubular body 30 may have an internal stop such as a localized narrowing in diameter to limit axial travel of a device. The sliding elongate tubular body 30 may have a tubular sleeve 30a that may also function as a stop as shown in FIG. 1H. A preferred embodiment is a proximal end reduction in diameter that prevents an embolic protection device from being drawn proximally out of the proximal end of the sliding elongate tubular body 30.

Elongate member 24 is preferably a wire; however, it may take the form of a metallic or non-metallic tube, strip, strand, or other structure having sufficient axial and torsional strength and stiffness to maintain functional orientation between proximal elongate tubular body 26 and distal elongate tubular body 28. Elongate member 24 may be embedded into the wall of proximal elongate tubular body 26 and distal elongate tubular body 28 (FIG. 1E) or may be attached to either the inner or outer surface thereof. All or part of elongate member 24 may be provided with means for chemical or mechanical attachment or interlock to proximal elongate tubular body 26 and distal elongate tubular body 28. For example, elongate member 24, proximal elongate tubular body 26, and/or distal elongate body 28 may be mechanically roughened such as by grit blasting or chemical etching, or may be provided with barbs, through holes, indentations, or other structures. Elongate member 24 may be provided with a primer coating to facilitate its attachment to proximal elongate tubular body 26 and distal elongate tubular body 28. Such a primer may comprise a chemical bonding agent, for example those used with adhesives, or may comprise a thin thermoplastic material known to provide good adhesion with elongate member 24 and with tubular body materials. Elongate member 24 can be attached to proximal elongate tubular body 26 and distal elongate tubular body 28 by adhesives, or can be heat fused into their walls, or can be incorporated into their walls during a dipping or spraying process, or by other means as known in the art. In a preferred embodiment, elongate member 24 extends over a portion of distal elongate tubular body 28 and does not extend to its tip.

It is contemplated that alternate structures can be used to attach proximal elongate tubular body 26 to distal elongate tubular body 28. For example, additional elongate members extending from proximal elongate tubular body 26 to distal elongate tubular body 28 can be provided (as shown in FIG. 1A). Partially coil wound wires (FIG. 1B), fabric such as braid, knit, weaves, in a single sheet or a sheet made from a tubular form in which the tubular form has been folded upon itself to form a two layer sheet (FIG. 1C), laser cut or etched tubular structures which may encircle or partially encircle the tubular body (FIG. 1D) can also be used to attach proximal elongate tubular body 26 to distal elongate tubular body 28. Preferably, these alternative structures are made of metal or engineering polymer, with NiTi being preferred.

Distal elongate tubular body 28 is comprised of a funnel shape as shown in the figures. Distal elongate tubular body 28 preferably is lined with a slippery material such as PTFE. Distal elongate tubular body 28 can be made from materials such as PEBAX, polyethylene, nylon, polyester, and alternatively can be dip or spray coated on mandrels (subsequently removed) from materials such as polyimide. Distal elongate tubular body 28 can be made from a tapered coil wound on a mandrel and subsequently coated with any of the polymers listed. In one embodiment, a tapered mandrel is first coated with polyimide containing a portion of PTFE, and subsequently coated with polyimide containing less or no PTFE. In another embodiment a non-tapered extruded material is flared by insertion of a tapered mandrel followed by a heat treatment to cause permanent expansion of a portion of the extruded tube. Alternatively, an extruded thermoplastic tube is surrounded by heat shrink tubing and compressed onto a tapered mandrel by applying sufficient heat to soften the extrusion and recover the heat shrink. In some embodiments, a portion of the funnel is formed by methods described above and a length of non-tapered tubing is attached to the distal end of the tapered portion using means known in the art.

Figure 2A:
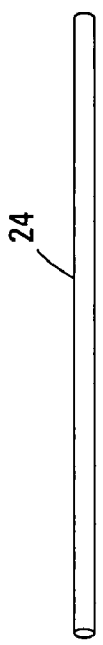
FIGS. 2A to 2D show a step in a process for making a catheter of the invention.
Figure 2B:
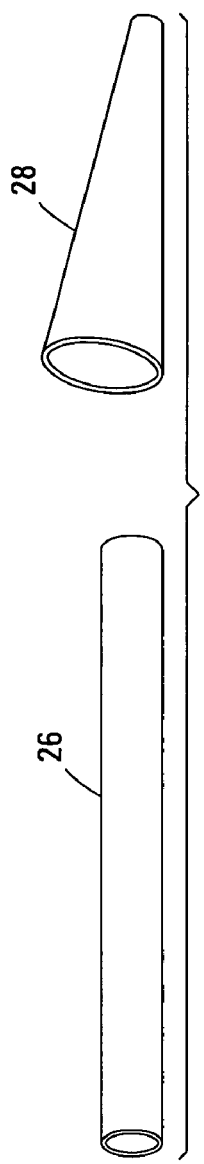
Figure 2C:
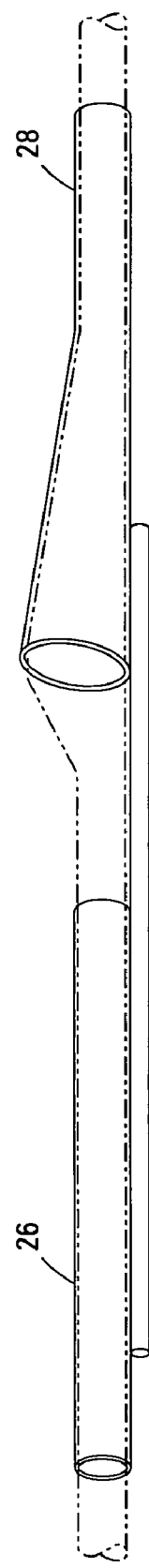
Figure 2D:
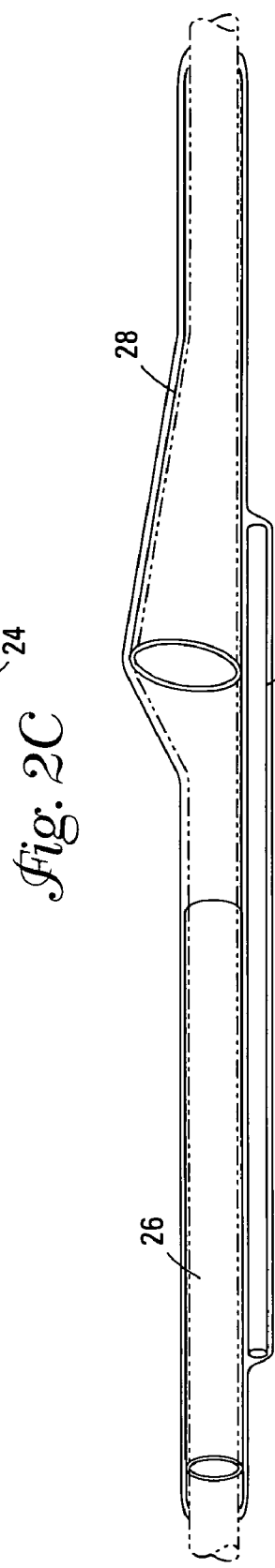

FIGS. 2A to 2D show a step in a process for making a catheter of the invention. A desired length of wire, such as stainless steel, is selected for the elongate member 24 (FIG. 2A). A desired length of a suitable tubular polymer resin, such as PEBAX® resin, is selected for the proximal elongate tubular body 26 and a tapered polymer segment as described above is selected for the distal elongate tubular body 28 (FIG. 2B). Nested mandrels, one with a tapered portion and one non-tapered, are inserted into the two tubes and the wire 24 is placed against the exterior of the 2 tubes. A suitable adhesive, such as LOCTITE®, is applied to the intersections of the two tubes with the wire (FIG. 2C). The arrangement of FIG. 2C is covered with one or more pieces of heat shrink material (FIG. 2D) and subjected to heat to reflow the polymer tubes. After the reflow process, the heat shrink material is removed, for example, by skiving, and the mandrels are removed.

Figure 1F:
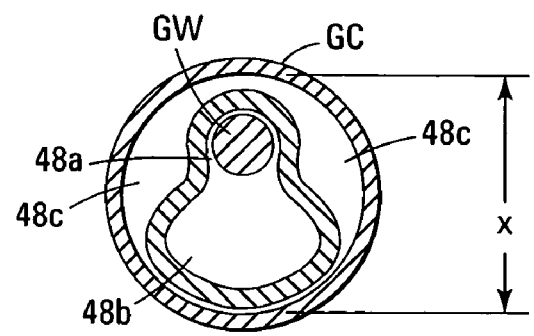
Figure 1G:
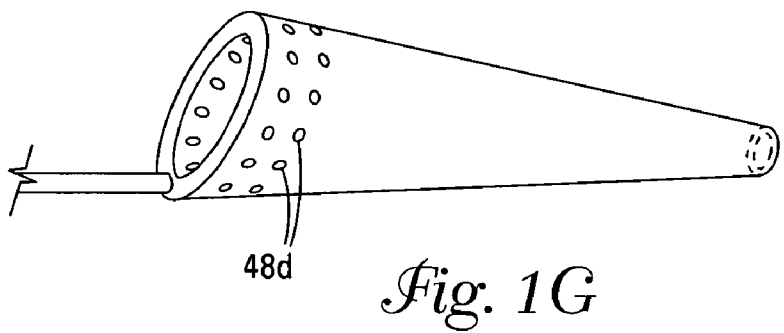
Figure 1H:
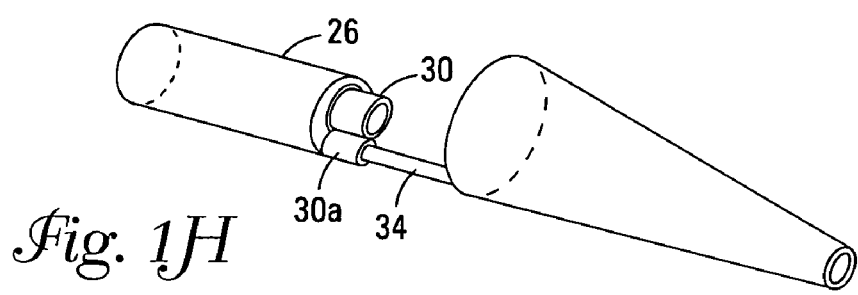

A portion of, and especially the proximal portion of distal elongate tubular body 28 may be non-circular in cross section as shown on FIG. 1F. A non-circular cross-section accommodates a lumen portion 48a for a guidewire GW, a lumen portion 48b for a device such as an embolic protection device (not shown), and space 48c within a guide catheter GC. Space 48c allows proximal end 48 of distal elongate tubular body 28 to be maximized in dimension "X" so as to accommodate both a guidewire and a device without causing proximal end 48 to function as a piston within guide catheter GC. Undesirable consequences of piston function include an inability to inject contrast dye through the guide catheter and around distal elongate tubular body 28, and inadvertent sucking of air into the guide catheter during distal advancement of distal elongate tubular body 28 though guide catheter. In an alternative embodiment, the proximal portion of distal elongate tubular body 28 is provided with perfusion holes 48d to solve the same problem (FIG. 1G). Holes 48d should be sized or shaped to not admit or otherwise interfere with the deployment or recovery of any portion of device such as a tip of an embolic protection device.

FIG. 1 in a preferred embodiment has hub 16 attached to proximal end as is well known to those skilled in the art. In embodiments where proximal tubular body 26 extends to proximal end of catheter 20, hub 16 can be affixed to the catheter proximal end to form a fluid-tight seal. Therapeutic coatings, including anti-thrombogenic coatings, for example heparin, or lubricious coatings, for example, hydrogels or silicone, can coat the delivery catheters of the invention.

Figure 3A:
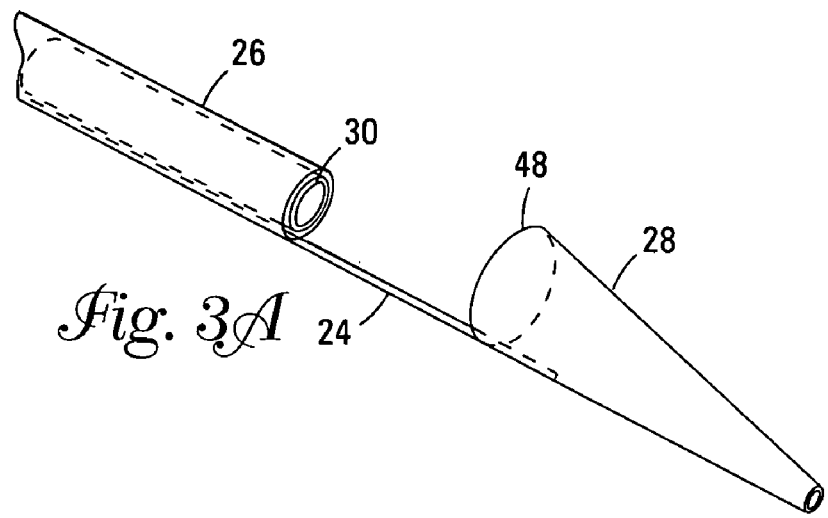
FIGS. 3A to 3C are perspective views of a catheter of the invention.
Figure 3B:
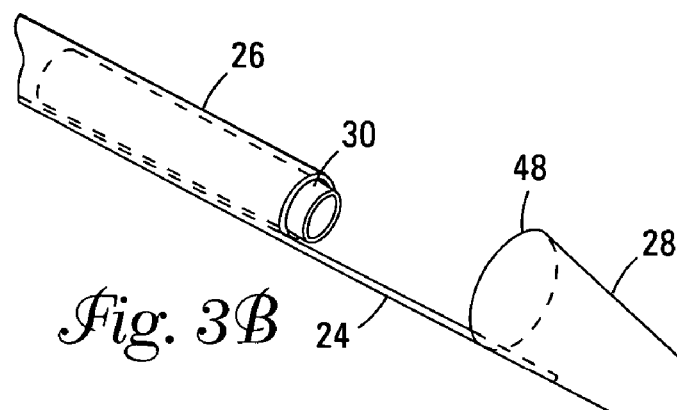
Figure 3C:
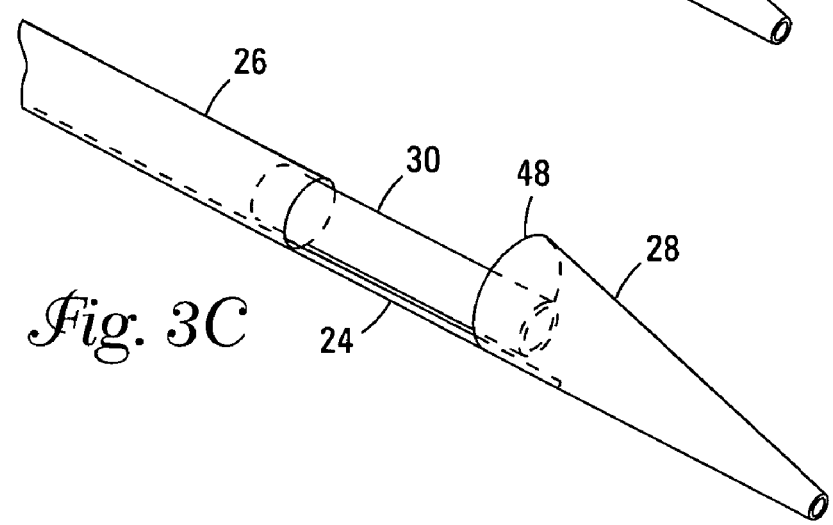

FIGS. 3A to 3C show the sliding elongate tubular body 30 moving from a position in which it is disposed entirely within the first elongate tubular body 26 to a position in which a portion of the sliding elongate tubular body 26 is disposed within the proximal portion of the second elongate tubular body 28.

FIGS. 4 to 6 show the use of the catheter of FIG. 3 with an embolic protection device 22. The embolic protection device 22 may be a filter. Other embolic protection elements which can be included as part of the present invention are occlusive emboli protection elements, including expandable or inflatable elements for blocking fluid flow through a vessel. Unless otherwise indicated, occlusive elements should be considered as interchangeable with filter elements in the present invention. Other embolic protection elements which can be included as part of the present invention are embolic protection elements intended to be placed proximal to, distal to, or at the site where emboli are generated. When the embolic protection device 22 is a filter, it will generally be in a compressed, radially reduced profile configuration as a result of disposition within the sliding elongate tubular body 30. Preferably, the filter is biased to expand radially outward when not constrained by the sliding elongate tubular body 30. Such filters are well known to those skilled in the art, as exemplified by filters disclosed in U.S. Pat. No. 6,325,815, U.S. 2002/0188314 A1, US 2003/0176884 A1, US 2003/0171770 A1, US 2003/0171771 A1, EP 1 181 900 A2, EP 1 226 795 A2, WO 01/15629 A1, WO 96/01591, and U.S. Ser. Nos. 10/354, 679, 10/354,829, and 10/354,831, each filed on Jan. 30, 2003, all of which are hereby incorporated by reference herein.

In one embodiment, the length of the proximal elongate tubular body 26 may be from 10 to 200 cm, and in another embodiment from 15 to 100 cm. In one embodiment, the length of the distal elongate tubular body 28 may be from 10 to 50 cm, and in another embodiment from 20 to 30 cm. In one embodiment, the length of the sliding elongate tubular body 30 may be from 3 to 15 cm, and in another embodiment from 5 to 10 cm.

To allow for ease of movement, the sliding tubular body exterior diameter should be less than the proximal tubular body interior diameter. The length of the elongate member 24 between the distal end 51 of the proximal elongate tubular body 26 and the proximal end 48 of the distal elongate tubular body 28 may be from 1 to 10 cm. The elongate member 24 may overlap the distal end 51 of the proximal elongate tubular body 26 and the proximal end 48 of the distal elongate tubular body 28 by a length of from 1 cm to its entire length and the two overlaps may be different. The proximal and sliding elongate tubular bodies may have a generally circular cross-sectional area along their length. The interior diameter D1 of the proximal elongate tubular body 26 may be from 0.02 to 0.10 inch and its wall thickness may be from 0.001 to 0.01 inch. The interior diameter D3 of the sliding elongate tubular body 30 may be from 0.01 to 0.09 inch, and its exterior diameter D4 may be from 0.02 to 0.10 inch. The distal elongate tubular body 28, or only the proximal end 48 thereof, may have a generally conical shape in which the cross-sectional area decreases along the axis from a larger cross-sectional area at the proximal end to a smaller cross-sectional area at the distal end. The interior diameter D2 of the proximal end 48 of the distal elongate tubular body 28 may be from 0.05 to 0.12 inch, and the interior diameter of the distal end 46 of the distal elongate tubular body 28 may be from 0.01 to 0.08 inch.

In one embodiment of the assembly of this invention, the guide wire 44 may be formed of stainless steel or nitinol or of a combination of materials and may have a safety, spring tip. Guide wire 44 can have a length of from 50 to 320 cm in some embodiments. Guide wire 44 may have radiopaque marker bands along its length. Guide wire 44 may also have an outside diameter of from 0.009 to 0.038 inches in some embodiments, and about 0.014 inches in a commonly used embodiment.

Optionally, a wire support structure 27 is disposed about the distal portion of the proximal elongate tubular body 26. This wire support structure may be in the form of a coil and may be of stainless steel. Suitably, the wire support structure may be made of ribbon wire of about 0.010 inch in wire width, 0.002 inch in wire thickness, by 10 cm long.

Materials well known to those skilled in the art can form the elongate tubular bodies. Polymers such as LDPE, MDPE, PEBAX®, nylon, or elastomeric polymers, such as polyurethane, silicone, latex, and the like, may be used to form a more flexible tubular body, while polymers such as HDPE, VESTAMID, or polyimide may be used to form a more rigid tubular body. A more flexible tubular body may be better adapted to advance through tortuous vessels while a more rigid body can provide pushability. The sliding elongate tubular body preferably is made of a more flexible material. The proximal elongate tubular body of the various embodiments may have an exterior surface compatible with hydrophilic coatings and may be so coated. The interior or exterior surfaces of the elongate tubular bodies may have lubricious surfaces to allow the medical device to move freely during deployment and to allow the proximal and sliding elongate bodies to move freely relative to each other.

In a suitable embodiment, a catheter of this invention may have the following parameters. The exterior diameter of the proximal tubular body may be less than 0.047 in. The wire support structure may be stainless steel wire dimensioned to 0.019 in. by 10 cm long. The interior of the proximal tubular body may be 0.038 in by 7.5 cm long. The proximal tubular body interior surface may have a lubricious lining, and its exterior surface may be compatible with hydrophilic coatings. The lumen of the sliding tubular body may be equal to or greater than 0.032 in by 7.5 cm. The exterior diameter of the sliding tubular body may suitably be less than the interior diameter of the proximal tubular body. The distal tubular body interior surface may have a lubricious lining and its exterior surface may be compatible with hydrophilic coatings. The interior diameter of the distal tubular body may transition from 0.032 in. at its distal end to 0.050 in. at its proximal end.

The catheter 20 may be provided to the physician or other end-user with a distal embolic protection device 22 preloaded but not retracted, as seen in FIG. 4A. In the as-provided position, the sliding tubular body 30 may be extended from or not extended from the proximal tubular body. To prepare the catheter 20 of FIG. 4A for positioning of the distal embolic protection device 22 at a target site within a patient's vasculature, the proximal end of the embolic protection device's elongate support member 32 is inserted into the distal end of distal elongate tubular body 28 and proximally advanced through sliding elongate tubular body 30 and proximal elongate tubular body 26. Further proximal motion of the embolic protection device's elongate support member 32 will retract distal embolic protection device 22 proximally within the distal elongate tubular body 28, as in FIG. 4B, and into the sliding elongate tubular body 30. Proximal end 34 of filter 22 will abut stop (not shown) within the sliding elongate tubular body 30, further proximal advancement of the embolic protection device's elongate support member 32 will draw the sliding elongate tubular body 30 proximally within the proximal elongate tubular body 26 until stops (not shown) on the sliding elongate tubular body 30 and proximal elongate tubular body 26 prevent further proximal retraction of the filter/sliding elongate tubular body combination, as in FIG. 4C.

The next step is for the doctor to position a guidewire 44 at or near a region of interest in a patient's vasculature. Guidewire 44 is then backloaded through the distal elongate tubular body 28 from the distal end 46 to the proximal end 48 of the distal elongate tubular body 28 and longitudinally along the proximal tubular body 26 exterior as shown in FIG. 5A. Next the catheter 20 is advanced along guidewire 44 until the tip 46 of distal elongate tubular body 28 is located at or near the target site within a patient's vasculature, for example, past a lesion L in a vessel V as shown in FIG. 5B. The guide wire 44 may now be withdrawn from the catheter and the patient, as shown in FIG. 5C by an arrow 50 in the direction for proximal withdrawal of the guide wire 44.

Figure 6A:
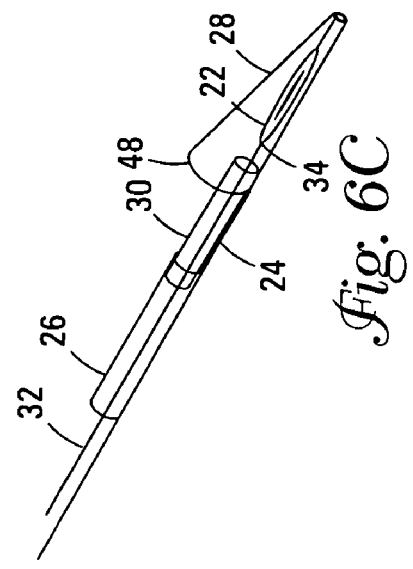
FIGS. 6A to 6C are perspective views of the catheter of FIG. 3 used to deploy an embolic protection device.
Figure 6B:
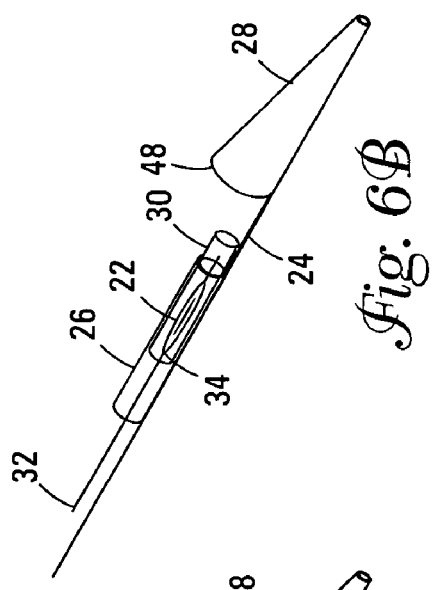
Figure 6C:
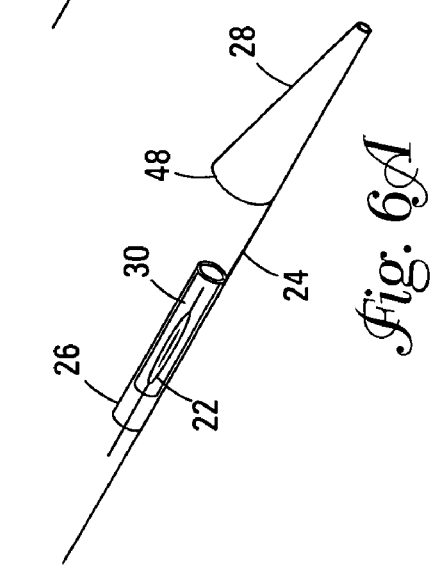

In FIGS. 6A to 6C, the guide wire 44 has been withdrawn from the catheter 20. FIGS. 6B and 6C show incremental advancement of the distal embolic protection device 22 distally within the sliding elongate tubular body 30 from the proximal elongate tubular body 26 to the distal elongate tubular body 28. The proximally extending elongate support member 32 of the distal embolic protection device 22 is advanced distally, and friction of the distal embolic protection device 22 against the interior of the sliding elongate tubular body 30 carries the sliding elongate tubular body 30 distally toward the distal elongate tubular body 28. Distal extension of the sliding elongate tubular body 30 may be limited by stops (not shown) as described earlier or by contact of the distal end of the sliding elongate tubular body 30 with the interior of the distal elongate tubular body 28.

When the sliding elongate tubular body 30 can advance no further into the distal elongate tubular body 28, the distal embolic protection device 22 advances into the distal elongate tubular body 28. Preferably, the distal embolic protection device 22 is now positioned past the lesion and within the catheter.

According to one embodiment, the catheter 20 is now proximally retracted. By retracting catheter 20, when the distal embolic protection device 22 is a filter, retraction of the assembly 20 allows the filter to expand radially, and preferably expand to provide filtration across the entire cross sectional area of the vessel. With the distal embolic protection filter in place, in some methods, the catheter 20 can be retracted from the patient. In other methods, the catheter 20 can remain in place, and a partially filled filter later retracted at least partially into the catheter 20 to close the filter mouth, and both filter and catheter retracted from the patient. In still other methods, the catheter 20 can be retracted from the patient, an interventional procedure performed over elongate support member 32, and the catheter 20 re-introduced over the shaft to recover the filter by closing at least the filter mouth.

Figure 7A:
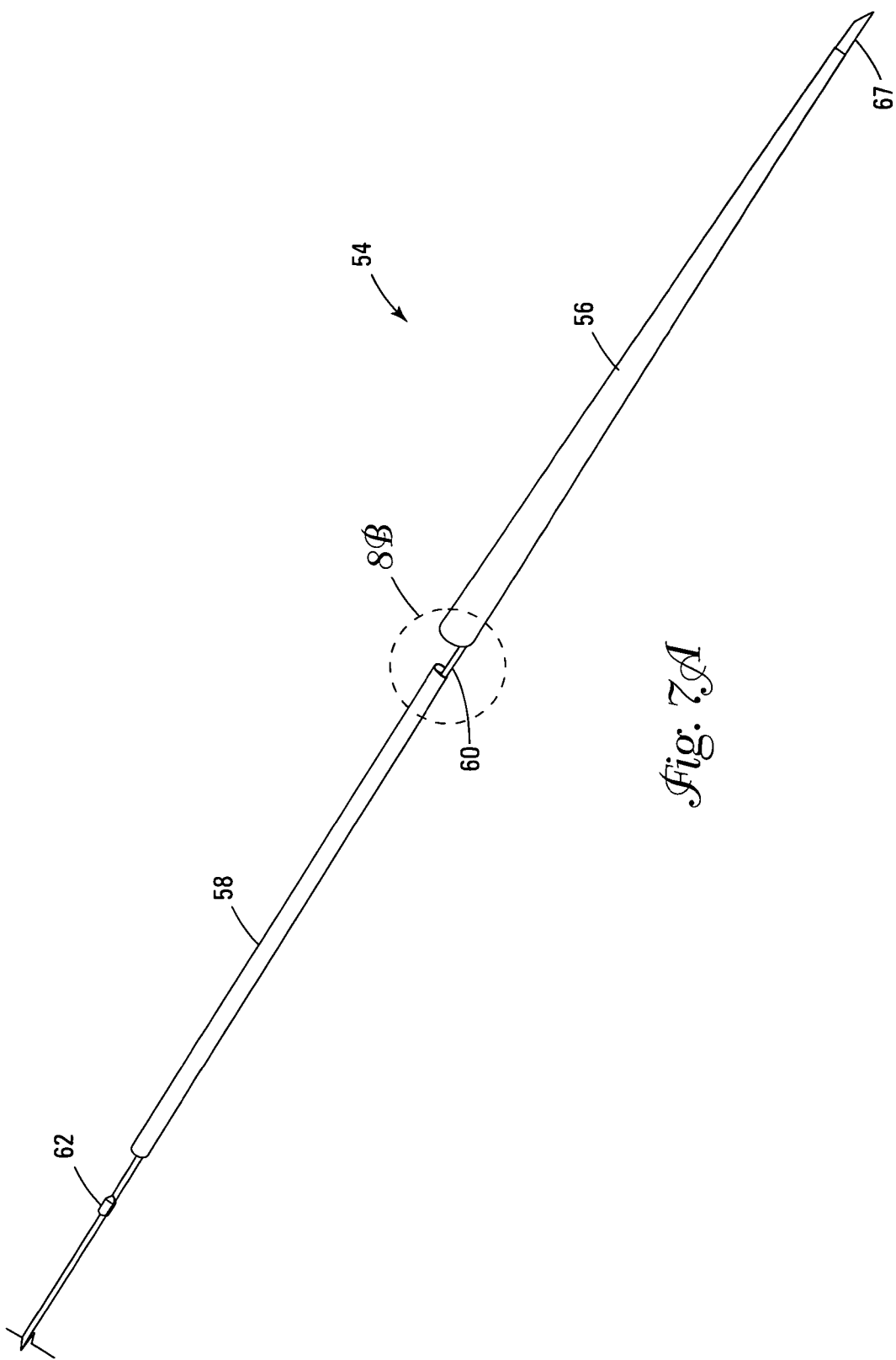

FIGS. 7A and 7B are perspective views of another embodiment of the catheter of the invention. According to the embodiment of FIG. 7A, the catheter 54 includes distal 56 and proximal 58 elongate tubular bodies, positioned longitudinally adjustably with respect to each other by an elongate member 60. Flexible tip 67 is disposed at the distal end of the distal elongate tubular body. Note that in the catheter 54 of this embodiment there is no third elongate tubular body, as in the catheter 20 of the preceding Figures. Note that the distal 56 and proximal 58 elongate tubular bodies are slidable relative to each other by the slidable connection of the elongate member 60 within the proximal elongate tubular body 58. Stop 62 may be provided on elongate member 60 to limit proximal motion of proximal elongate tubular body 58. Stop 62 may be comprised of a solder bead or a band of metal or polymer material affixed to elongate member 60. One or more stops may be added to elongate member 60 to limit its motion, or proximal portion of elongate member can be enlarged to limit proximal motion of proximal tube. Elongate member 60 is preferably not round but can be a flattened wire or multi wires can be used to substantially prevent rotation of the two bodies. Alternatively, proximal elongate tubular body 58 may comprise a bellows or an axially stretchable material. Distal end of proximal elongate tubular body 58 may have a protruding portion 64 that can enter the distal elongate tubular body and that may contact same during distal advancement of proximal elongate tubular body 58 (FIG. 7B).

The catheter 54 is used in methods similar to those described above. The guide wire can exit the distal and proximal ends of the distal elongate tubular body 56 and be positioned longitudinally along the exterior of the proximal elongate tubular body 58. The guide wire can be removed after the catheter is positioned. Proximal elongate tubular body 58 can be slid over support member 60 to allow deployment of device 22. An embolic protection device can then be advanced through the distal elongate tubular body 56.

The distal elongate tubular body 28 or 56 of catheter 20 or 54, respectively, may include a distally tapering outer diameter over the distal region (not shown). The distal end diameter need only be large enough to pass a guide wire and the distal embolic protection device, for example, between from 0.01 to 0.09 inch.

The tubular bodies may translate, telescope and otherwise move with respect to each other. The translating tubular bodies of the various assembly embodiments may be made bi- or multi-stable to retain desired configurations, according to the preference of the treating physician. Magnetic or mechanical latching mechanisms may retain the various tubular bodies in a particular relationship to each other, the chosen medical device and the therapeutic procedure.

FIG. 8A is a perspective view of another embodiment of the catheter of the invention. According to the embodiment of FIG. 8A, the catheter 90 includes distal 92 and proximal 94 elongate tubular bodies, positioned longitudinally adjustably with respect to each other by an elongate member 96. Proximal and distal tubes may be two lumen tubes with cross sections similar to those shown in FIGS. 8B and 8C. Proximal tube 94 may include stop 98 (similar to stops described above). Optionally, a sliding tube (not shown) can be provided. Device 22 is prepositioned in proximal tube 94. Construction materials and methods like those described above for the other embodiments can be used for this embodiment.

Also shown in FIG. 8A is removable guidewire introducer 900 comprised of hub 902 and shaft 904. Hub 902 is conventional to the art, and shaft 904 is a flexible polymer or a metal, conventional in the art. The introducer is optional.

In use, catheter 90 is used in the same manner as described above. Introducer 900 can be pre-placed in catheter 90 distal tube 92 so that when a guidewire is backloaded into catheter 90 it can simply be loaded into distal end of introducer shaft 904 and exit hub 902, thus minimizing the chances for the proximal end of the guidewire to inadvertently enter proximal tube 94. Introducer 900 is removed before catheter 90 is advanced into the patient.

Figure 9:
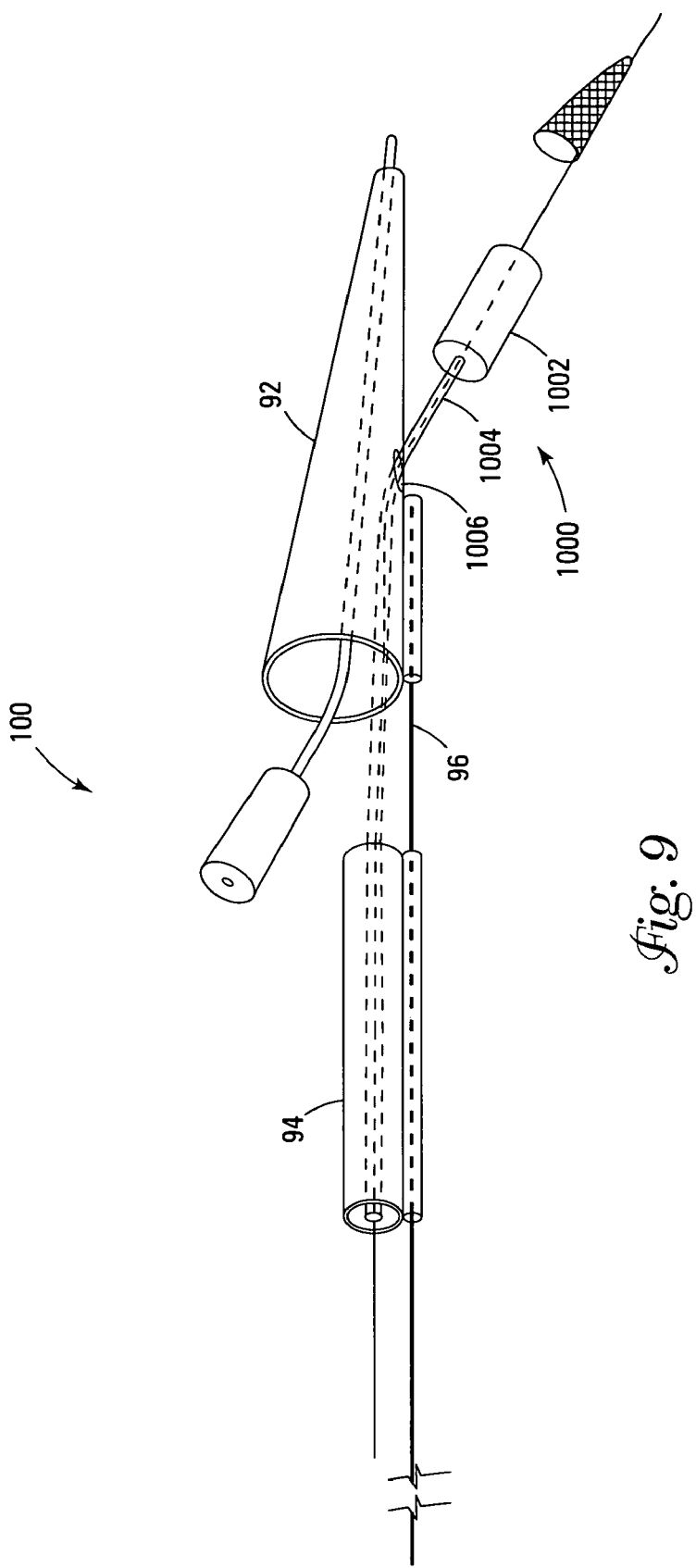
FIG. 9 is a perspective view of an embodiment of a catheter of the invention.

FIG. 9 is a perspective view of another embodiment of the catheter of the invention. Catheter 100 is similar to catheter 90 except sideport 1006 has been added to accommodate device introducer 1000. Device introducer 1000 is comprised of hub 1002 and shaft 1004. Hub 1002 is conventional to the art, and shaft 1004 is a flexible polymer or a metal, conventional in the art. The introducer is optional.

In use, catheter 100 is used in the same manner as described above. Introducer 1000 can be pre-placed in catheter 100 distal tube 92 so that when the device is backloaded into catheter 100 it can simply be loaded into hub 1002 of introducer 1000 and exit shaft 1004, thus maximizing the chances for the proximal end of device wire to enter the proximal tube. Introducer 1000 is removed before catheter 100 is advanced into the patient. Of course, one could decide to use both, either, or neither introducer.

Figures 10A, 10B, 10C:
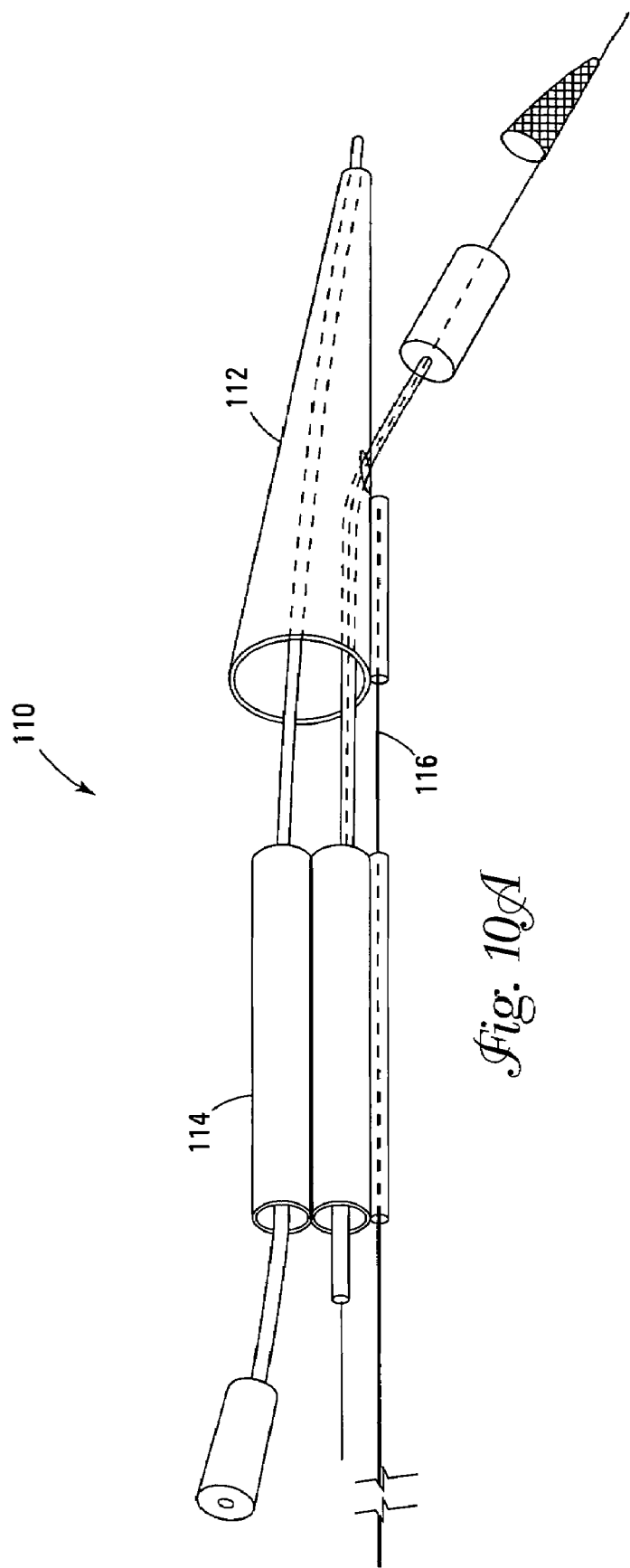
FIGS. 10A to 10C are views of another embodiment of a catheter of the invention.

FIG. 10A is a perspective view of another embodiment of the catheter of the invention. According to the embodiment of FIG. 10A, the catheter 110 includes distal 112 and proximal 114 elongate tubular bodies, positioned longitudinally adjustably with respect to each other by an elongate member 116. Distal tube 112 may be a two-lumen tube with cross sections similar to those shown in FIGS. 8B and 8C. Proximal tube 114 may be a three-lumen tube with cross sections similar to those shown in FIGS. 10B and 10C. Proximal tube 114 device lumen may include a stop (similar to stops described above). Optionally, a sliding tube (not shown) can be provided within the proximal tube 114 device lumen. Device 22 is prepositioned in proximal tube 114. Construction materials and methods like those described above for the other embodiments can be used for this embodiment. Introducers are preferably used as drawn.

Figure 11:
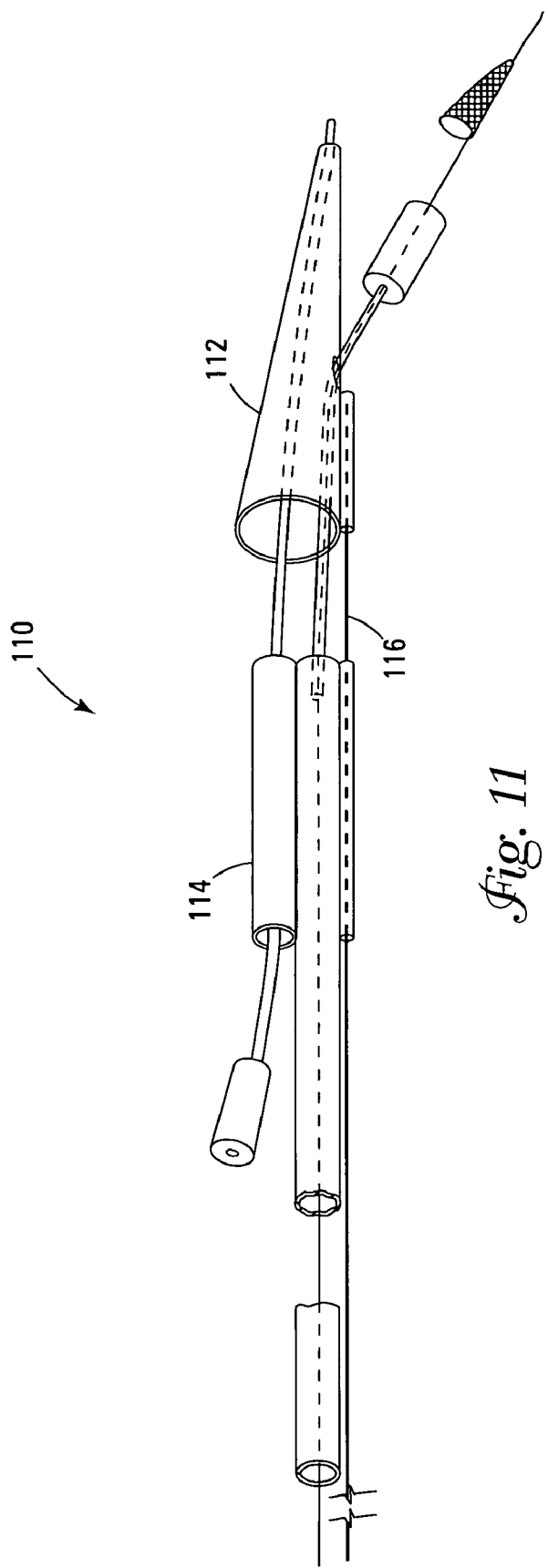
FIG. 11 is a perspective view of another embodiment of a catheter of the invention.

FIG. 11 is a perspective view of another embodiment of the catheter of the invention. FIG. 11 is similar to FIG. 10A, except the proximal tube device wire lumen has been extended proximally to a proximal hub that resides outside of the patient. The proximal tube and elongate member optionally can be bonded or otherwise attached. The extended proximal tube can be slit or slotted. See the slotted catheter configuration in U.S. Ser. No. 10/171,704, filed Jun. 14, 2002, and entitled "Rapid Exchange Catheters Usable with Embolic Protection Devices", the contents of which are hereby incorporated by reference herein. Alternatively the extended proximal tube can be provided with a tear away lumen. See U.S. Ser. No. 10/460,750, filed Jun. 12, 2003, entitled "Catheter with Removable Wire Lumen Segment", the contents of which are hereby incorporated by reference herein. Use of the slotted and removable segment catheters is described more fully in these two applications.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A catheter assembly comprising:
   a first elongate tubular body having a proximal portion, a distal portion, a proximal end having a proximal opening, a distal end having a distal opening, and a lumen extending between the proximal opening and the distal opening;
   a second elongate tubular body having a proximal portion, a distal portion, a proximal end having a proximal opening, a distal end having a distal opening, and a lumen extending between the proximal opening and the distal opening; and
   an elongate member joining the first and second elongate bodies,
   the first elongate tubular body being disposed proximal and tandem to the second elongate tubular body, and the first and second tubular bodies being permanently disposed so that the first and second tubular bodies are not adjacent to each other,
further comprising a third elongate tubular body having a proximal portion, a distal portion, a proximal end having a proximal opening, a distal end having a distal opening, and a lumen extending between the proximal opening and the distal opening,
a medical device contained within the lumen of the third elongate tubular body,
at least the proximal portion of the third elongate tubular body being disposed within the lumen of the first elongate tubular body, the third elongate tubular body being slidable within the lumen of the first elongate tubular body, and
the distal portion of the third elongate tubular body being sized to be disposed in the lumen of the second elongate tubular body,
the third elongate tubular body being moveable over a limited range of motion from a proximal position where the distal end of the third elongate tubular body is proximal of the proximal end of the second elongate tubular body to a distal position where the distal end of the third elongate tubular body is distal of the proximal end of the second elongate tubular body,
the medical device being moveable from the lumen of the third elongate tubular body to the lumen of the second elongate tubular body when the third elongate tubular body is in the distal position,
wherein the proximal end of the third elongate tubular body is maintained within the lumen of the first elongate tubular body over the entire limited range of motion.

2. A catheter of claim 1, wherein the entire third elongate tubular body is sized to be disposed within the lumen of the first elongate tubular body.

3. A catheter of claim 1, wherein the first elongate tubular body has an inner diameter and the elongate member has one or more transverse cross-sectional dimensions, each transverse cross-sectional dimension being less than half the inner diameter of the first elongate tubular body.

4. A catheter of claim 3, wherein each transverse cross-sectional dimension is less than one-quarter of the inner diameter of the first elongate tubular body.

5. A catheter of claim 1, wherein the catheter comprises a single elongate member.

6. A catheter of claim 1, wherein the catheter comprises two or more elongate members.

7. A catheter of claim 1, wherein the elongate member is a curved sheet that partially encircles the first and second tubular bodies.

8. A catheter of claim 7, wherein the curved sheet is made of knit, a weave, or tubular braid that has been folded upon itself to form a sheet.

9. A catheter of claim 1, wherein at least a portion of the second elongate tubular body has a non-circular transverse cross-section.

10. A catheter of claim 1, wherein the second elongate tubular body has one or more holes disposed in its proximal portion.

11. A catheter of claim 1, wherein the elongate member is cylindrical.

12. A catheter of claim 1, wherein the second elongate tubular body has an inner diameter that decreases from the proximal end to the distal end of the second elongate tubular body.

13. A catheter of claim 1, wherein the second elongate tubular body is funnel-shaped.

14. A catheter of claim 1, wherein a proximal shaft is attached to the first elongate tubular body.

15. A catheter of claim 14, wherein the proximal shaft is cylindrical.

16. A catheter of claim 14, wherein the proximal shaft and the elongate member are formed of one cylindrical element.

17. A catheter of claim 1, wherein the first elongate tubular body has a length of from 10 to 200 cm.

18. A catheter of claim 17, wherein the first elongate tubular body has a length of from 15 to 100 cm.

19. A catheter of claim 1, wherein the second elongate tubular body has a length of from 10 to 50 cm.

20. A catheter of claim 19, wherein the second elongate tubular body has a length of from 20 to 30 cm.

21. A catheter of claim 1, wherein the third elongate tubular body has a length of from 3 to 15 cm.

22. A catheter of claim 21, wherein the third elongate tubular body has a length of from 5 to 10 cm.

23. A catheter of claim 1, wherein the first elongate tubular body has an inner diameter of from 0.02 to 0.10 inch.

24. A catheter of claim 1, wherein the second elongate tubular body has an inner diameter of from 0.01 to 0.12 inch.

25. A catheter of claim 1, wherein the third elongate tubular body has an outer diameter of from 0.02 to 0.10 inch.

26. A catheter of claim 1, wherein the third elongate tubular body has an inner diameter of from 0.01 to 0.09 inch.

27. A catheter of claim 1, wherein the distance between the distal end of the first elongate tubular body and the proximal end of the second elongate tubular body is from 1 to 10 cm.

28. A catheter of claim 1, wherein the catheter is selected from a balloon catheter, an infusion/dye-injection/suction catheter, stent delivery catheter, or an embolic protection device delivery catheter.

29. A catheter of claim 28, wherein the catheter is a balloon catheter.

30. A catheter of claim 28, wherein the catheter is an infusion/dye-injection/suction catheter.

31. A catheter of claim 28, wherein the catheter is a stent delivery catheter.

32. A catheter of claim 28, wherein the catheter is an embolic protection device delivery catheter.

33. A catheter of claim 1, wherein the catheter comprises an interventional element on the second elongate tubular body.

34. A catheter of claim 1, wherein the first and second elongate tubular bodies are formed of one or more polymers.

35. A catheter of claim 1, wherein the second elongate tubular body has a side wall extending between its proximal and distal ends and a port disposed on the side wall.

36. A catheter assembly comprising:
a first elongate tubular body having a proximal portion, a distal portion, a proximal end having a proximal opening, a distal end having a distal opening, and a lumen extending between the proximal opening and the distal opening;
a second elongate tubular body having a proximal portion, a distal portion, a proximal end having a proximal opening, a distal end having a distal opening, and a lumen extending between the proximal opening and the distal opening; and
an elongate member joining the first and second elongate bodies,
the first elongate tubular body being disposed proximal and tandem to the second elongate tubular body, and the first and second tubular bodies being permanently disposed so that the first and second tubular bodies are not adjacent to each other, further comprising a third elongate tubular body having a proximal portion, a distal portion, a proximal end having a proximal opening, a distal end having a distal opening, and a lumen extending between the proximal opening and the distal opening, a medical device contained within the lumen of the third elongate tubular body, at least the proximal portion of the third elongate tubular body being disposed within the lumen of the first elongate tubular body, the third elongate tubular body being slidable within the lumen of the first elongate tubular body, wherein the third tubular body is configured to move between a first proximal position and a second distal position, the distal end of the third elongate tubular body being between the distal end of the first tubular body and the proximal end of the second tubular body when the third elongate tubular body is in the first proximal position and being within the lumen of the second tubular body when the third elongate tubular body is in the second distal position, wherein the proximal end of the third elongate tubular body is maintained within the lumen of the first elongate tubular body when the third elongate tubular body is in the first proximal position and when the third elongate tubular body is in the second distal position, and the medical device being moveable from the lumen of the third elongate tubular body to the lumen of the second elongate tubular body when the third elongate tubular body is in the second distal position.

37. A catheter of claim 36, wherein the entire third elongate tubular body is sized to be disposed within the lumen of the first elongate tubular body.

38. An assembly for delivering a catheter, the assembly comprising a guide wire and a catheter, the catheter having a proximal portion and a distal portion comprising:

a first elongate tubular body having a proximal portion, a distal portion, a proximal end having a proximal opening, a distal end having a distal opening, and a lumen extending between the proximal opening and the distal opening;

a second elongate tubular body having a proximal portion, a distal portion, a proximal end having a proximal opening, a distal end having a distal opening, and a lumen extending between the proximal opening and the distal opening; and an elongate member joining the first and second elongate bodies, the first elongate tubular body being disposed proximal and tandem to the second elongate tubular body, and the first and second tubular bodies being permanently disposed so that the first and second tubular bodies are not adjacent to each other, further comprising a third elongate tubular body having a proximal portion, a distal portion, a proximal end having a proximal opening, a distal end having a distal opening, and a lumen extending between the proximal opening and the distal opening, the third elongate tubular body having a length less than a length of the first elongate tubular body, and a medical device contained within the lumen of the third elongate tubular body, the third elongate tubular body being slidable within the lumen of the first elongate tubular body, the third elongate tubular body being moveable over a limited range of motion from a proximal position where the distal end of the third elongate tubular body is proximal of the proximal end of the second elongate tubular body to a distal position where the distal end of the third elongate tubular body is within the lumen of the second elongate tubular body and where the proximal end of the third elongate tubular body is within the lumen of the first elongate tubular body, the medical device being moveable from the lumen of the third elongate tubular body to the lumen of the second elongate tubular body when the third elongate tubular body is in the distal position.

39. An assembly comprising an embolic protection device and a catheter, the catheter having a proximal portion and a distal portion comprising:

a first elongate tubular body having a proximal portion, a distal portion, a proximal end having a proximal opening, a distal end having a distal opening, and a lumen extending between the proximal opening and the distal opening;

a second elongate tubular body having a proximal portion, a distal portion, a proximal end having a proximal opening, a distal end having a distal opening, and a lumen extending between the proximal opening and the distal opening; and an elongate member joining the first and second elongate bodies, the first elongate tubular body being disposed proximal and tandem to the second elongate tubular body, and the first and second tubular bodies being permanently disposed so that the first and second tubular bodies are not adjacent to each other, further comprising a third elongate tubular body having a proximal portion, a distal portion, a proximal end having a proximal opening, a distal end having a distal opening, and a lumen extending between the proximal opening and the distal opening, the lumen of the third elongate tubular body being sized to contain the embolic protection device, at least the proximal portion of the third elongate tubular body being disposed within the lumen of the first elongate tubular body, the third elongate tubular body being slidable within the lumen of the first elongate tubular body, wherein the third tubular body is configured to be slideable from a first position where the second and third tubular bodies are not abutting each other to a second position where the second and third tubular bodies are abutting each other, the embolic protection device being moveable from the lumen of the third elongate tubular body to the lumen of the second elongate tubular body when the third elongate tubular body is in the second position, and wherein the proximal end of the third elongate tubular body is maintained within the lumen of the first elongate tubular body in both the first and second positions.

40. A method for positioning a catheter assembly within a patient's blood vessel, the method comprising:

providing a catheter, the catheter having a proximal portion and a distal portion comprising:

a first elongate tubular body having a proximal portion, a distal portion, a proximal end having a proximal opening, a distal end having a distal opening, and a lumen extending between the proximal opening and the distal opening;

a second elongate tubular body having a proximal portion, a distal portion, a proximal end having a proximal opening, a distal end having a distal opening, and a lumen extending between the proximal opening and the distal opening; and an elongate member joining the first and second elongate bodies, the first elongate tubular body being disposed proximal and tandem to the second elongate tubular body, and the first and second tubular bodies being permanently disposed so that the first and second tubular bodies are not adjacent to each other, further comprising a third elongate tubular body having a proximal portion, a distal portion, a proximal end having a proximal opening, a distal end having a distal opening, and a lumen extending between the proximal opening and the distal opening, and a medical device contained within the lumen of the third elongate tubular body, at least the proximal portion of the third elongate tubular body being disposed within the lumen of the first elongate tubular body, the third elongate tubular body being slidable within the lumen of the first elongate tubular body, and the distal portion of the third elongate tubular body being sized to be disposed in the lumen of the second elongate tubular body, the third elongate tubular body being moveable over a limited range of motion from a proximal position where the distal end of the third elongate tubular body is proximal of the proximal end of the second elongate tubular body to a distal position where the distal end of the third elongate tubular body is distal of the proximal end of the second elongate tubular body, wherein the proximal end of the third elongate tubular body is maintained within the lumen of the first elongate tubular body over the entire limited range of motion;

providing a guide wire having a proximal end and a distal end;

advancing the guide wire to a target site within the patient's blood vessel;

disposing the guide wire proximal end within the lumen of the second elongate tubular body and not within the lumen of the first elongate tubular body;

advancing the catheter over the guide wire to the target site;

moving the third elongate tubular body from the proximal position to the distal position; and after the third elongate tubular body is moved to the distal position moving the medical device from the lumen of the third elongate tubular body to the lumen of the second elongate tubular body.

41. A method of claim 40, wherein the guide wire is removed from the catheter after the catheter has been advanced to the target site.

42. A method of claim 41, further comprising, after the catheter has been advanced to the target site, advancing an interventional medical device through the lumens of the first and second elongate tubular bodies to the target site.

43. A method of claim 42, wherein the interventional medical device is an embolic protection device.

44. A method of claim 40, wherein the entire third elongate tubular body is able to be disposed within the lumen of the first elongate tubular body.

45. A method of claim 40, wherein the first elongate tubular body has an inner diameter and the elongate member has one or more transverse cross-sectional dimensions, each transverse cross-sectional dimension being less than half the inner diameter of the first elongate tubular body.

46. A method of claim 45, wherein each transverse cross-sectional dimension being less than one-quarter of the inner diameter of the first elongate tubular body.

47. A method of claim 40, wherein the catheter comprises a single elongate member.

48. A method of claim 40, wherein the catheter comprises two or more elongate members.

49. A method of claim 40, wherein the elongate member is a curved sheet that partially encircles the first and second tubular bodies.

50. A method of claim 49, wherein the curved sheet is made of knit, a weave, or tubular braid that has been folded upon itself to form a sheet.

51. A method of claim 40, wherein at least a portion of the second elongate tubular body has a non-circular transverse cross-section.

52. A method of claim 40, wherein the second elongate tubular body has one or more holes disposed in its proximal portion.

53. A method of claim 40, wherein the elongate member is cylindrical.

54. A method of claim 40, wherein the second elongate tubular body has an inner diameter that decreases from the proximal end to the distal end of the second elongate tubular body.

55. A method of claim 40, wherein the second elongate tubular body is funnel-shaped.

56. A method of claim 40, wherein a proximal shaft is attached to the first elongate tubular body.

57. A method of claim 56, wherein the proximal shaft is cylindrical.

58. A method of claim 56, wherein the proximal shaft and the elongate member are formed of one cylindrical element.

59. A method of claim 40, wherein the catheter is selected from a balloon catheter, an infusion/dye-injection/suction catheter, stent delivery catheter, or an embolic protection device delivery catheter.

60. A method of claim 59, wherein the catheter is a balloon catheter.

61. A method of claim 59, wherein the catheter is an infusion/dye-injection/suction catheter.

62. A method of claim 59, wherein the catheter is a stent delivery catheter.

63. A method of claim 59, wherein the catheter is an embolic protection device delivery catheter.

64. A method of claim 40, wherein the catheter comprises an interventional element on the second elongate tubular body.

65. A method of claim 40, wherein the first and second elongate tubular bodies are formed of one or more polymers.

66. A method of claim 40, wherein the second elongate tubular body has a side wall extending between its proximal and distal ends and a port disposed on the side wall.

67. A method for positioning a catheter assembly within a patient's blood vessel, the method comprising:

providing a catheter, the catheter having a proximal portion and a distal portion comprising:

a first elongate tubular body having a proximal portion, a distal portion, a proximal end having a proximal opening, a distal end having a distal opening, and a lumen extending between the proximal opening and the distal opening;

a second elongate tubular body having a proximal portion, a distal portion, a proximal end having a proximal opening, a distal end having a distal opening, and a lumen extending between the proximal opening and the distal opening; and an elongate member joining the first and second elongate bodies, the first elongate tubular body being disposed proximal and tandem to the second elongate tubular body, and the first and second tubular bodies being permanently disposed so that the first and second tubular bodies are not adjacent to each other, further comprising a third elongate tubular body having a proximal portion, a distal portion, a proximal end having a proximal opening, a distal end having a distal opening, and a lumen extending between the proximal opening and the distal opening, at least the proximal portion of the third elongate tubular body being disposed within the lumen of the first elongate tubular body, the third elongate tubular body being slidable within the lumen of the first elongate tubular body, wherein the third tubular body is configured to move between a first proximal position and a second distal position, the distal end of the third elongate tubular body being between the distal end of the first tubular body and the proximal end of the second tubular body when the third elongate tubular body is in the first proximal position and being within the lumen of the second tubular body when the third elongate tubular body is in the second distal position, providing a medical device contained within the lumen of the third elongate tubular body, and wherein the proximal end of the third elongate tubular body is maintained within the lumen of the first elongate tubular body when the third elongate tubular body is in the first proximal position and when the third elongate tubular body is in the second distal position;

providing a guide wire having a proximal end and a distal end;

advancing the guide wire to a target site within the patient's blood vessel;

disposing the guide wire proximal end within the lumen of the second elongate tubular body and not within the lumen of the first elongate tubular body; and advancing the catheter over the guide wire to the target site;

moving the third elongate tubular body from the proximal position to the distal position; and after the third elongate tubular body is moved to the distal position moving the medical device from the lumen of the third elongate tubular body to the lumen of the second elongate tubular body.

* * * * *